United States Patent [19]
Leuchter et al.

[11] Patent Number: 5,269,315
[45] Date of Patent: Dec. 14, 1993

[54] DETERMINING THE NATURE OF BRAIN LESIONS BY ELECTROENCEPHALOGRAPHY

[75] Inventors: Andrew F. Leuchter, Los Angeles; Ian A. Cook, Beverly Hills, both of Calif.

[73] Assignee: The Regents of the University of California, Oakland, Calif.

[21] Appl. No.: 745,872

[22] Filed: Aug. 16, 1991

[51] Int. Cl.$^5$ .......................... A61B 5/0476
[52] U.S. Cl. .................................. 128/731
[58] Field of Search ....................... 128/731, 732

[56] References Cited

U.S. PATENT DOCUMENTS

| | | | |
|---|---|---|---|
| 4,579,125 | 4/1986 | Strobl et al. | 128/731 |
| 4,800,895 | 1/1989 | Moberg et al. | 128/731 |
| 4,846,190 | 7/1989 | John | 128/731 |

OTHER PUBLICATIONS

Mary J. De Leon, Ajax E. George, Jeffrey D. Miller, et al., "Altered Patterns of Positron-Emission Tomography Glucose Metabolism in Alzheimer Patients with Microvascular White Matter Disease," in *American Journal of Physiologic Imaging* (vol. 3: 1988, pp. 52–53).

Andrew F. Leuchter, M.D. and Donald O. Walter, Ph.D., "Diagnosis and Assessment of Dementia using Functional Brain Imaging," *International Psychogeriatrics* (vol. 1: 1, 1989, pp. 63–72).

Sheldon E. Jordan, Ralph Nowacki, and Marc Nuwer, "Computerized Electroencephalography in the Evaluation of Early Dementia," *Brain Topography* (vol. 1: 4, 1989, pp. 271–282).

Barry S. Oken, M.D., Keith H. Chiappa, M.D., and Martin Salinsky, M.D., "Computerized EEG Frequency Analysis: Sensitivity and Specificity in Patients with Focal Lesions," in *Neurology* (vol. 39: Oct. 1989, pp. 1281–1287).

Andrew Leuchter, M.D., James E. Spar, M.D., Donald Walter, M.D., et al., "Electroencephalographic Spectra and Coherence in the Diagnosis of Alzheimer's-Type and Multi-infarct Dementia," in *Archives of General Psychiatry* (vol. 44: Nov. 1987, pp. 993–998).

J. Breslau, A. Starr, N. Sicotte, et al., "Topographic EEG changes with normal aging and SDAT," in *Electronencephalography and Clinical Neurophysiology* (vol. 72: 1989, pp. 281–289).

V. E. Pollock, L. S. Schneider and S. A. Lyness, "EEG amplitudes in healthy, late-middle-aged and elderly adults: normality of th distributions and correlations with age," in *Electroencephalography and Clinical Neurophysiology* (vol. 75: 1990, pp. 276–288).

Fernando Torres, Angelina Faoro, Ruth Loewenson et al., "The Electroencephalogram of Eldery Subjects Revisited," *Electroencephalography and Clinical Neurophysiology* (vol. 56: 1983, pp. 391–398).

M. Onofri, D. Gambi, G. Malatesta et al., "Electrophysiological Techniques in the Assessment of Aging Brain: Lacunar State and Differential Diagnosis," in *Neuroepidemology*, vol. 29: 1989, (Suppl. 2).

Hellmuth Lechner, Reinhold Schmidt, Bertha Goetz, "Long-Term Experience of a Trial in Multi-Infarct Dementia," in *Neuroepidemiology* (vol. 9: 1990, pp. 228–232).

(List continued on next page.)

Primary Examiner—William E. Kamm
Assistant Examiner—Scott M. Getzow
Attorney, Agent, or Firm—Sheldon & Mak

[57] ABSTRACT

Determining brain lesions by quantified electroencephalography is effected by obtaining absolute power data in a primary frequency domain for a brain region. Power data in the primary frequency domain in relation to power in a secondary frequency domain is determined. The two sets of data are related to obtain a value representative of the electrical output in the brain region. The representative value is compared to a selected base value and quantified departures are mapped topographically. This map is used to identify and assess lesions associated with disorders and afflictions including dementia and demyelinating diseases.

52 Claims, 12 Drawing Sheets

OTHER PUBLICATIONS

Gastone G. Celesia, "EEG and Event-Related Potentials in Aging and Dementia," in *Journal of Clinical Neurophysiology* (vol. 3: 2, 1986, pp. 99–111).

Ch. Logar, W. Grabmair, G. Schneider et al., "EEG changes in senile dementia of Alzheimer-type," *Z. EEG-EMG* (German Research Journal) (vol. 18: 1987, pp. 214–216).

"QSI 9000–The Complete Electrodiagnostic System," *Quantified Signal Imaging Inc.*, Outario (Advertisement Brochure).

"Letters on Brain Mapping," in *Clinical EEG Electroencephalography*, (vol. 21:2, 1990, pp. 7–10).

David Loring, Daniel E. Sheer and John W. Largen, "Forty Hertz EEG Activity in Dementia of the Alzheimer Type and Multi-Infarct Dementia," in *Psychophysiology* (vol. 22: 1, pp. 116–121).

T. Erkinjuntti, T. Larsen, R. Sulkava et al., "EEG in the differential diagnosis between Alzheimer's disease and vascular dementia," in *Acta Neurological Scandananvia* (vol. 77: 1988, pp. 36–43).

Leslie Prichep, Francisco Gomez Mont, E. Roy Hohn et al., "Neurometric Electroencephalographic Characteristics of Dementia," (Book chapter, title unknown, pp. 252–257).

Richard P. Brenner, Richard F. Ulrich, Duane G. Spiker et al., "Computerized EEG Spectral Analysis in Elderly Normal, Demented and Depressed Subjects," in *Electroencephalography and Clinical Neurophysiology* (vol. 64: 1986, pp. 483–492).

K. P. O'Connor, J. C. Shaw and C. O. Ongley, "The EEG and Differential Diagnosis in Psychogeriatrics," in *British Journal of Psychiatry* (vol. 135: 1979, pp. 156–162).

Lawrence A. Coben, Warren Danziger and Martha Storandt, "A Longitudinal EEG Study of Mild Senile Dementia of Alzheimer Type Changes as 1 Year and at 2.5 Years," in *Electroencephalography and Clinical Neurophysiology* (vol. 61: 1985, pp. 101–112).

Lawrence A. Coben, Warren L. Danziger, and Leonard Berg, "Frequency Analysis of the Resting Awake EEG in Mild Senile Dementia of Alzheimer Type," in *Electroencephalography and Clinical Neurophysiology* (vol. 55: 1983, pp. 372–380).

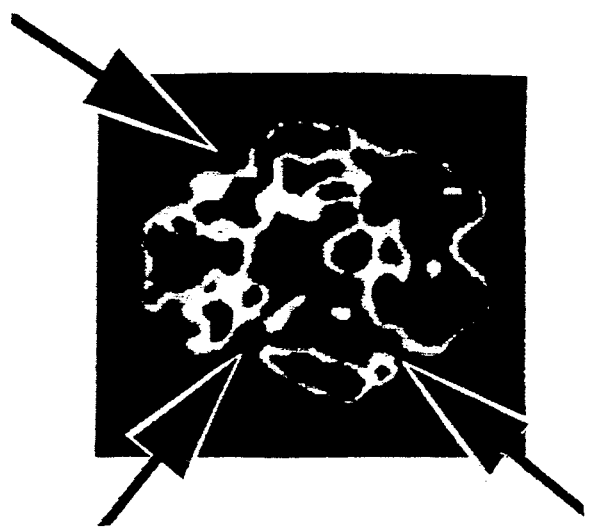
FIG. IC
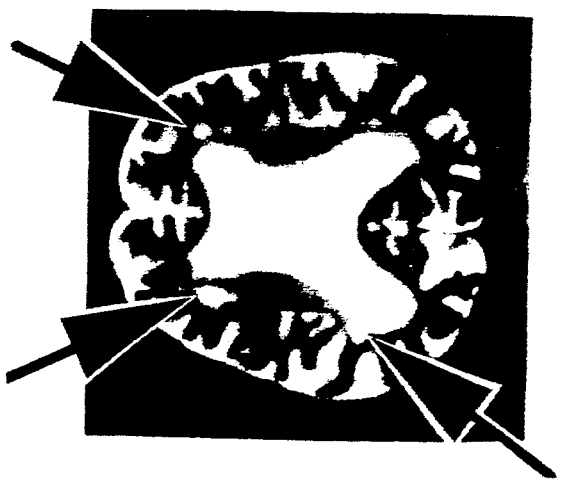
FIG. IB
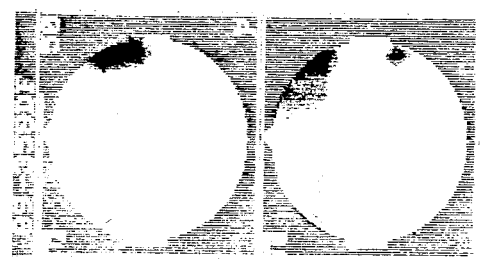
DELTA
THETA
FIG. IA

ALZHEIMER'S DISEASE

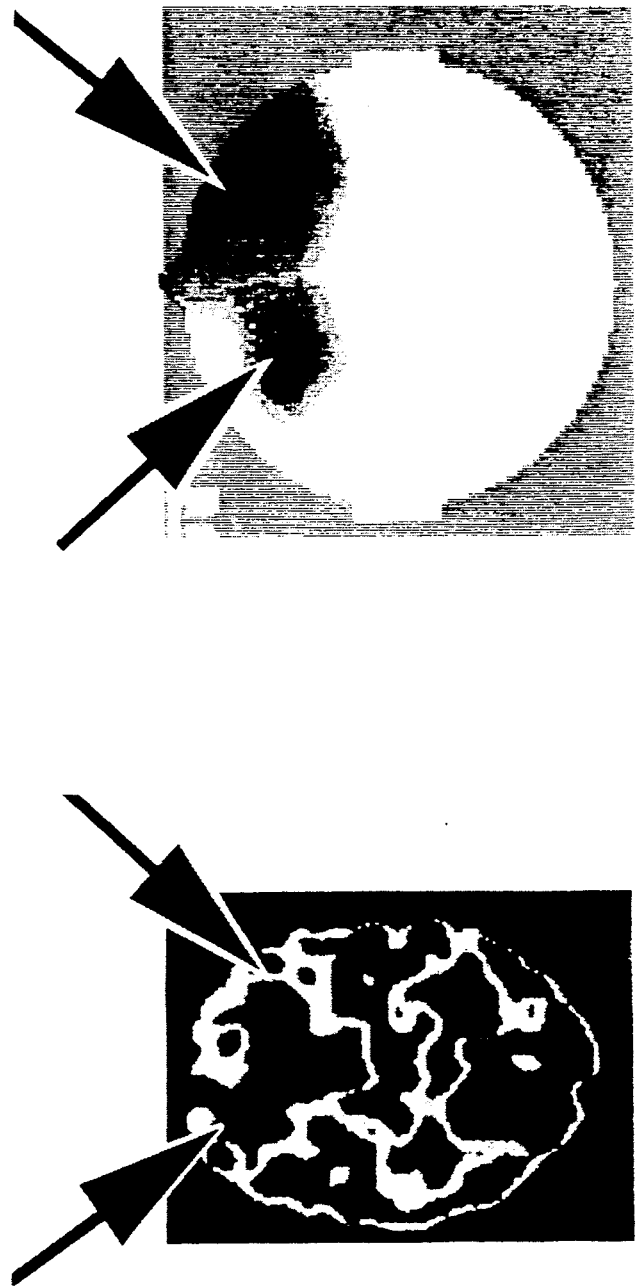

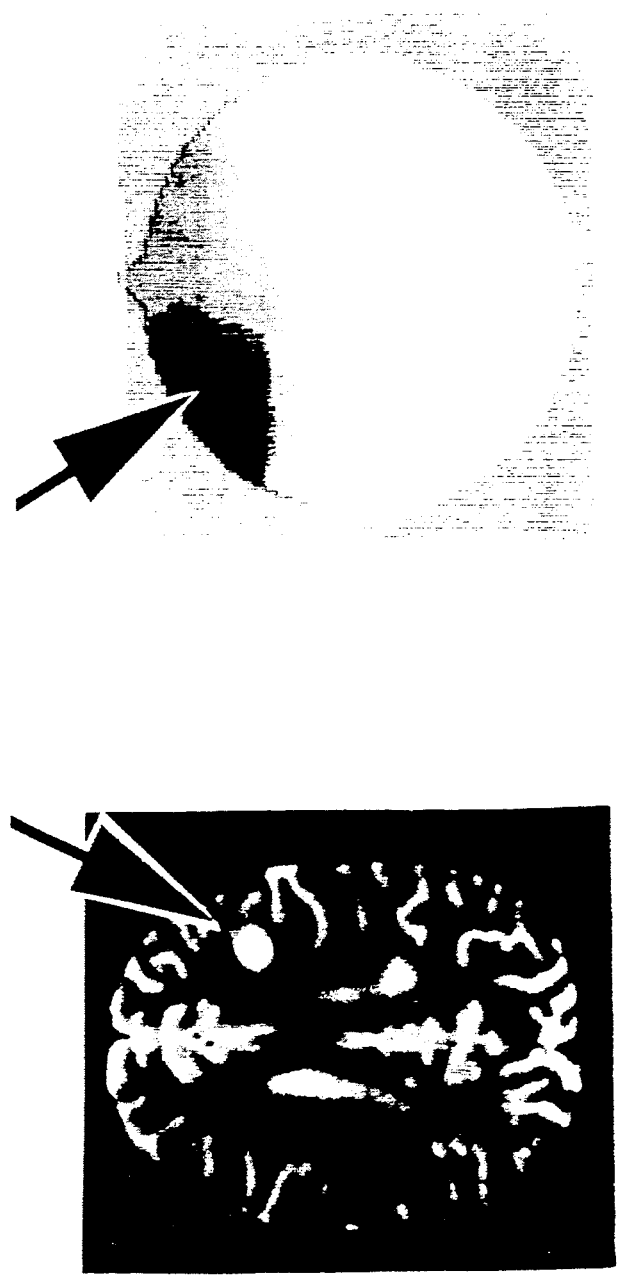

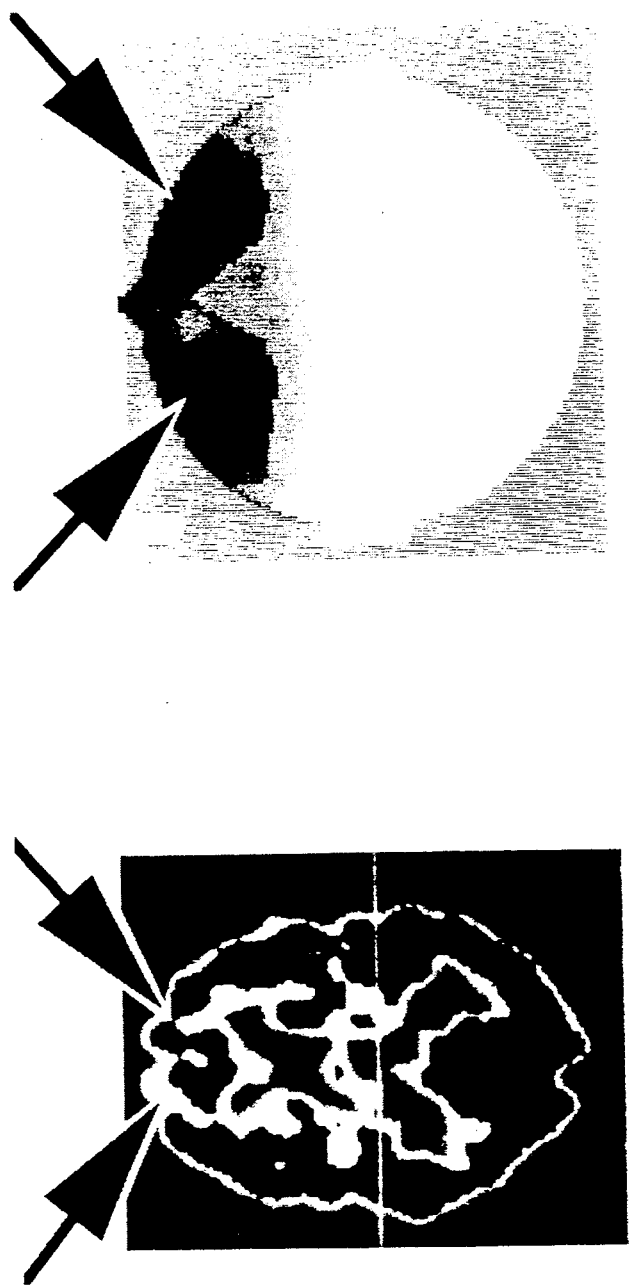

DETERMINING THE NATURE OF BRAIN LESIONS BY ELECTROENCEPHALOGRAPHY

Portions of the work leading to this application were developed under a grant of the National Institute of Mental Health (NIMH) under Grant No. MH 40705. The NIMH may have rights in this application.

BACKGROUND

Diagnosing disorders and afflictions in the human brain with non-invasive procedures is important medically and scientifically.

This invention relates to determining the nature of brain lesions using quantitative electrophysiology. In particular, the invention relates to analyzing electroencephalographic information in a manner to permit assessment of the nature of brain lesions. The invention is further directed to give a characterization of afflictions such as dementia, being selective for multi-infarct dementia or Alzheimer's disease, Pick's disease and demyelinating diseases such as multiple sclerosis.

Brain imaging used by physicians in clinical practice includes structural imaging and functional imaging. Structural imaging is effected by computed axial tomography (CAT) scanning or magnetic resonance imaging (MRI) scanning. Functional imaging is effected by positron emission tomography (PET), single photon emission computed tomography (SPECT) or electroencephalography (EEG).

Structural imaging is performed for determining the location of a brain tumor or other kind of gross structural alteration of the brain. Functional imaging tests are performed to determine functional alteration in the brain where there may not be significant structural alteration. These broad categories of tests are complementary. A physician evaluating a neurological or psychiatric illness could perform a test from both categories to assess and/or diagnose a patient's condition. The present invention particularly concerns functional imaging.

PET scanning measures brain metabolism and can identify areas that are hypoactive. SPECT scanning measures cerebral blood flow, which is an indirect measure of metabolism and therefore brain function. Both of these technologies yield useful physiological information. For example, Alzheimer's disease presents with hypometabolism or hypoperfusion of the parietal lobes bilaterally and multi-infarct dementia presents with multiple foci of hypometabolism and hypoperfusion. PET and SPECT scanning are expensive, requiring investments of millions of dollars initially. Also required are many hours of technician time per test and the production and injection of radionuclides into a patient.

EEG brain mapping is relatively less expensive and can be performed without the need for radionuclides. Technician time for performing the scan also is less costly. A disadvantage of EEG mapping, however, is that it has not been possible to analyze the information obtained by the electroencephalogram to diagnose and assess effectively different conditions of the brain, and thus diseases and disorders of the brain.

Information which is obtainable from an EEG includes conventional EEG data representative of electrical activity in different brain regions. When this data is digitized and processed as in quantitative EEG ("qEEG"), it is possible to obtain topographical brain mapping of electrical activity in different brain regions. From a qEEG unit, it is also possible to obtain measurements of absolute power and relative power, and evoked potentials. Quantitative EEG techniques represent an advance over traditional EEG methods because they permit the detection of trends which are difficult or impossible to discern by direct visual inspection of the EEG voltage tracings. Previous efforts to generate images depicting quantitative EEG data have had limited clinical applicability because they have not been shown convincingly to be associated with specific clinical syndromes or diagnoses; for example, the presence of a qEEG brain map of regions with large amounts of power in the delta band may reflect an electrophysiologic encephalopathy from many diseases, without distinguishing between them.

A shortfall of all these EEG and qEEG data and information which are analyzed independently is the inability to provide information regarding brain physiology that is substantially equivalent to information from PET or SPECT scans.

SUMMARY

By the present invention, there is provided a method and means of minimizing the disadvantages of EEGs and providing for enhanced techniques of quantitative EEG analysis. The invention provides for information about brain electrical function that can be associated with specific diseases and syndromes and thus can assist in establishing different diagnoses.

According to the invention, the determination of the electrical output of a brain region comprises obtaining first data representative of energy in the brain region in a primary frequency domain. Second data representative of energy in the primary frequency domain relative to the energy in a secondary frequency domain are determined substantially simultaneously.

The first data and the second data are then related, thereby obtaining a representative value of the electrical output in the brain region. This relationship is established on the combination of the first data and the second data.

The representative value obtained by this combination of first data and second data is a concordance value or a discordance value. Such values are quantified relative to the departure of the first data and second data from a simultaneously obtained selected base value. The concordance value is indicated by departure of both the first data and the second data in a first direction from a selected base value. A discordance value is indicated by departure of the first data and the second data in opposite directions from a selected base value.

Preferably, the concordance value and discordance value are quantified and mapped topographically relative to the brain region. The mapping is effected in selected frequency domains and is employed to assess and assist diagnosing disorders and afflictions characterized by lesions in the brain. This mapping is referred to as cordance brain mapping.

The first data and second data are selectively absolute power and relative power, respectively. Absolute power is a determination of the intensity of electric activity in a given frequency domain in a brain region. Relative power is a measure of the proportion of electrical activity in a given frequency domain in a brain region. Cordance mapping represents an enhancement of quantified EEG methods that adds significant sensitivity for at least the detection of deep or cortical brain lesions.

The invention provides for information about brain electrical function that can be associated with specific diseases and thus can distinguish between different diagnoses.

The invention covers the method of determining the electrical output in regions of the brain, apparatus for providing the determination, and the use of such methodology and apparatus to perform assessments and characterization of the human brain.

The invention is now further described with reference to the accompanying drawings.

DRAWINGS

FIG. 1 includes three views of scans of a patient with multi-infarct dementia. FIG. 1A is a brain map illustrating discordance in the two frequency bands in a linked ear montage; FIG. 1B is an MRI scan illustrating the same brain region; and FIG. 1C is a SPECT scan illustrating the same brain region as the brain map.

FIG. 2 includes three views of scans of the same patient as in FIG. 1. FIG. 2A is a brain map illustrating concordance in the one frequency band in a linked ear montage; FIG. 2B is an MRI scan illustrating the same brain region; and FIG. 2C is a SPECT scan illustrating the same brain region.

FIG. 3 includes three views of scans of a patient with dementia of unknown etiology. FIG. 3A is a brain map illustrating discordance in the one frequency band in a linked ear montage; FIG. 3B is an MRI scan illustrating the same brain region; and FIG. 3C is an MRI scan illustrating the same brain region.

FIG. 4 includes two views of scans of a patient with Alzheimer's disease. FIG. 4B is a brain map illustrating discordance in the one frequency band in a reformatted bipolar montage, herein termed bipolar montage; FIG. 4A is a PET scan illustrating the same brain region.

FIG. 5 includes two views of scans of a patient with Pick's disease. FIG. 5B is a brain map illustrating discordance in the one frequency band in a bipolar montage; FIG. 5A is a SPECT scan illustrating the same brain region.

FIG. 6 are further brain scans of the patient illustrated in FIG. 5. In FIG. 6A, there is illustrated absolute power in four frequency bands; FIG. 6B illustrates relative power in four frequency bands; FIG. 6C illustrates discordance maps in four frequency bands; and FIG. 6D illustrates concordance maps in four frequency bands. FIGS. 6A and 6B are obtained in a linked ear montage; FIGS. 6C and 6D are obtained in a bipolar montage.

FIG. 7 includes two views of scans of a patient with multiple sclerosis. FIG. 7B is a brain map illustrating discordance in the one frequency band in a bipolar montage; FIG. 7A is an MRI scan illustrating the same brain region.

FIG. 8 includes two views of scans of a control subject with white-matter disease. FIG. 8B is a brain map illustrating discordance in the one frequency band in a bipolar montage; FIG. 8A is a SPECT scan illustrating the same brain region.

Figure 2C:
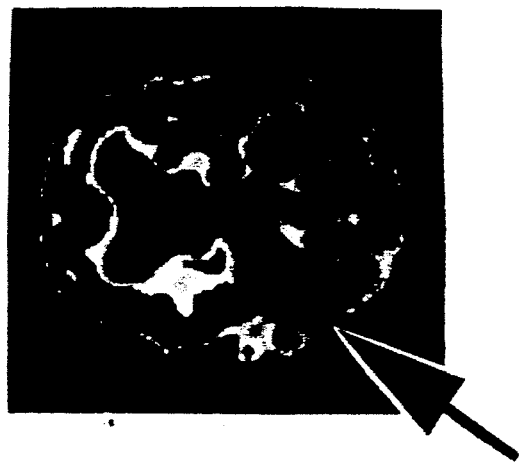

FIG. 11 are brain scans of the patient illustrated in FIG. 1 and 2. In FIG. 11A, there is illustrated absolute power in four frequency bands; FIG. 11B illustrates relative power in four frequency bands; FIG. 11C illustrates discordance maps in four frequency bands; and FIG. 11D illustrates concordance maps in four frequency bands. FIGS. 11A and 11B are obtained in a linked ear montage; FIGS. 11C and 11D are obtained in a bipolar montage.

FIG. 12 are brain scans of the patient illustrated in FIG. 1 and 2, the relationship being in a linked ear montage. In FIG. 12A, there is illustrated absolute power in four frequency bands; FIG. 12B illustrates relative power of four frequency bands; 13 FIG. 12C illustrates discordance maps in four frequency bands; and FIG. 12D illustrates concordance maps in four frequency bands.

DESCRIPTION

Determining the electrical output of the brain region of a subject and hence the assessment or diagnosis of a disorder or affliction of the brain as characterized by a lesion comprises obtaining first data representative of the energy intensity in the brain region in a primary frequency domain. These data are represented by the absolute power in the primary frequency domain which is defined by specific frequency bands. These are the conventional four frequency bands, namely, delta, theta, alpha, and beta frequency bands of electrical activity.

From these first data, there are determined second data, namely, the relative power, which is representative of energy in a selected primary frequency domain relative to the energy in a secondary frequency domain.

While the primary frequency domain is any one of the frequency bands delta, theta, alpha and beta, the secondary frequency domain can comprise one or more than one frequency band.

In some cases, the primary frequency domain is several of the frequency bands and the secondary frequency domain is a different frequency band or set of bands which should preferably incorporate at least part of the frequency band or bands of the primary frequency domain.

The absolute power and relative power are related to obtain a representative value of the electrical output in the brain region. Relating is effected by determining the absolute power and relative power compared to a selected base value. When the first data and the second data both increase or decrease relative to a selected base value, a concordance condition is indicated. When one of the first data and the second data respectively increase or decrease relative to the selected base while the other of the first data or second data respectively is oppositely directed relative to the selected base, a discordance condition is indicated.

The relationship of the absolute power and relative power is then established. When the absolute power and relative power are both greater than a selected base value, then a quantified concordance value is calculated, indicated and displayed. Similarly, when one of the absolute powers and relative powers are oppositely directed relative to the selected base value, then a quantified discordance value is calculated, indicated and displayed.

The indicated and displayed values provide the indices of concordance and discordance that are related to the presence of brain lesions. The distribution of concordance and discordance values in the brain region is displayed topographically through cordance mapping.

Thereby, there is obtained a spatial distribution and information relating to the pathophysiological nature of the brain lesions. Through this technique, the evaluation of disorders and afflictions characterized by lesions can be assessed to assist in a diagnosis. Typical of the diseases and disorders that can be determined are dementing illnesses such as multi-infarct dementia, Alzheimer's disease and Pick's disease, demyelinating diseases such as multiple sclerosis, as well as lesions among otherwise healthy control subjects.

The delta frequency band is conventionally the slowest frequency, being from about 0 Hz to 4 Hz; theta is from about 4 Hz to 8 Hz; alpha is from about 8 Hz to 12 Hz; and beta is from about 12 Hz and higher, namely, to about 20 Hz or 30 Hz in frequency.

In the exemplified version of the invention, the primary frequency domain incorporates any one of these bands. The selected secondary frequency domain includes all of the delta, theta, alpha and beta frequency bands.

The first data is the absolute power. It is indicated in microvolts squared and indicates the energy intensity in a selected single frequency band ("primary frequency domain"). The second data is relative power. It is representative of the energy in a selected single frequency band relative to all the frequency bands ("secondary frequency domain"). The relative power represents a fraction of, or the percentage of, power in the selected single frequency band relative to the absolute power in all frequency bands.

In the determination of the electrical output of a brain region of the head of the subject, an objective base value is first established for each subject. This objective base is conveniently a selected base being a midpoint for the absolute power and a selected base being a midpoint for the relative power for each subject. It is a midpoint of a normalized base value of 1 which is representative of the respective maximum absolute power and the maximum relative power. The maximum absolute power and maximum relative power are selected values of the first data and the second data, respectively. Values other than the maximum can be selected as necessary.

Figure 9:
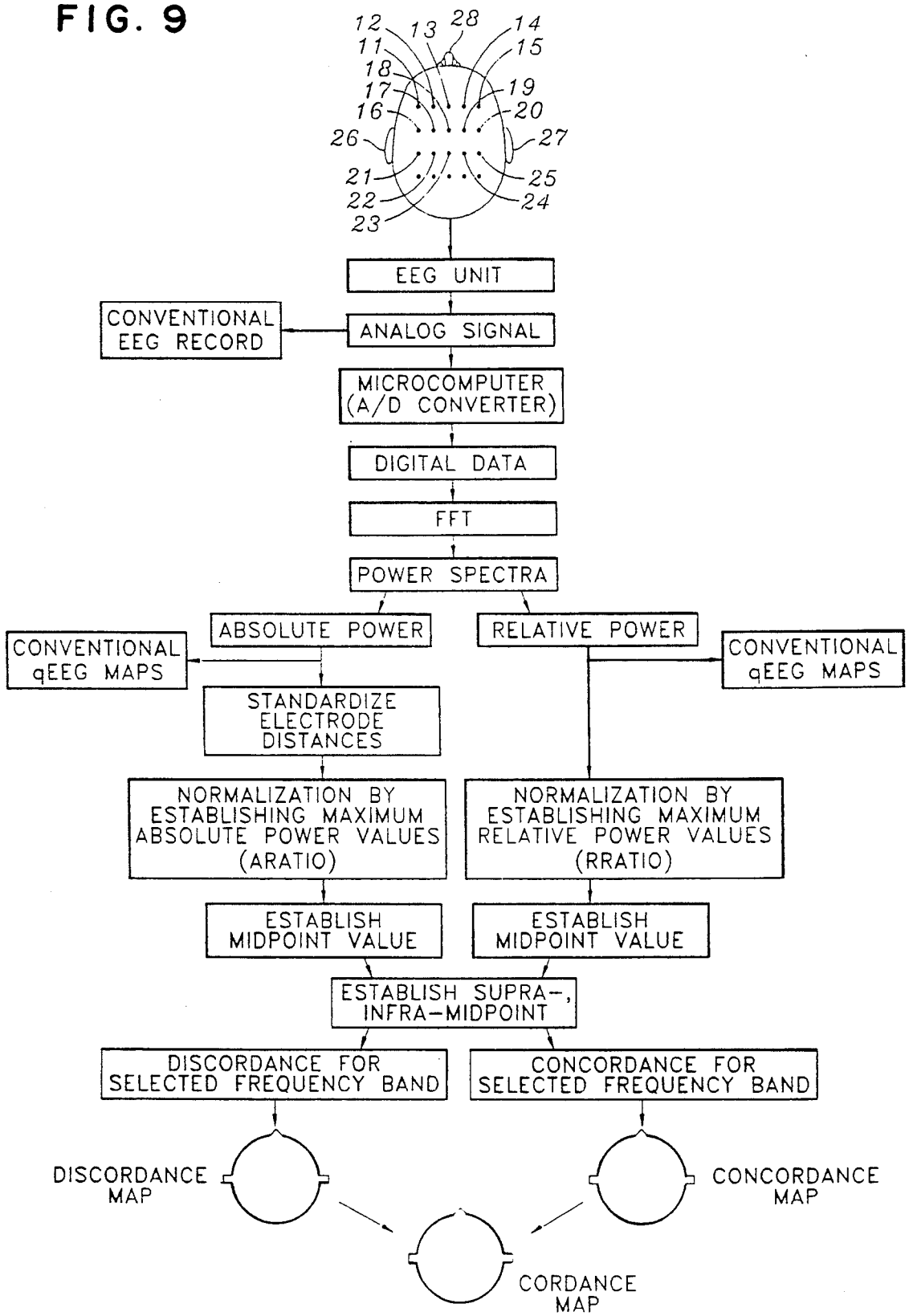
FIG. 9 is a schematic of major components illustrating the data processing and flow to obtain the cordance map from the electrical output in a brain region.

As indicated in FIG. 9, the energy distribution is sensed and measured by electrodes located on the head of a patient to obtain analog signals in each electrode for an EEG unit. Each pair of recording electrodes establishes a channel. The analog signal provides a conventional EEG waveform record as indicated. The analog signal is digitized by the A/D converter in a microcomputer to become digital data. A Fast Fourier Transform (FFT) process is applied to the digital data to yield absolute power values for respective EEG channels. The relative power also is calculated. These channels represent each of about 20 electrodes located strategically about the head of a patient. The absolute power values and the relative power values each serve independently to provide conventional EEG brain maps as indicated. Such brain maps would otherwise be termed as quantitive EEGs.

With reference to the objective base value which is established for each subject, the maximum absolute power and the maximum relative power is set up for the values across all channels for each frequency band.

The absolute power data and the relative power data are used in combination in accordance with the invention to establish representative values to permit cordance mapping. The absolute power value serves as a basis for determining concordance and discordance calculations which characterize the quantity and quality of the electrical output of the brain region. This is taken in the context of energy from recording locations of all electrode channels and in all the frequency bands.

The absolute power values are processed by computer means into relative power values by dividing, for each channel, the amount of power present in a given frequency band by the total power for each channel. Relative power thus reflects the distribution of the energy for a channel among the different frequency bands. There can thus be an absolute power value and a relative power value for each frequency band for each of the electrodes located about the head.

The absolute power and relative power values are normalized by division by the maximum absolute and maximum relative power values, respectively, across all 20 channels and each of the four frequency bands. The maximum absolute power value and the maximum relative power values are determined by examining the absolute and relative power values for each channel, and selecting the greatest absolute power value and greatest relative power value. These normalized ratios or values are called respectively the "aratio" and "rratio" and are compared with the maximum values normalized to 1.0 ("normalized base"). This comparison yields the concordance and discordance quantification. These procedures are effected by appropriate computing and microprocessing means programmed to effect the requisite data calculations and processing.

A channel exhibits a discordant pattern and is quantified with a discordance value when the absolute power is diminished relative to its selected base value while the relative power is increased in relation to its selected base value. A selected base value is specifically defined as a percentage, fraction, or proportion of the normalized value 1 ("normalized base"). In a discordant condition, the aratio is less than "$\frac{1}{2}$ of the maximum absolute power" ("selected base") and the rratio is greater than "$\frac{1}{2}$ of the maximum relative power" ("selected base").

In this sense, the normalized value is a "normalized" base, and the midpoint or half point of the base is a "selected base" or proportionate value representative of that normalized base value. The quantified discordance value or score is determined by the sum of the deviation of the absolute power from "$\frac{1}{2}$ of its base value" ("selected base") and the deviation of the relative value from "$\frac{1}{2}$ of its base value" ("selected base"), as can be expressed by the form:

$$\text{discordance score} = (\text{rratio} - 0.5) + (0.5 - \text{aratio})$$

A large discordance score describes the condition of a channel with a low power signal that is confined mostly to a given frequency band.

Should the absolute power and relative power both be increased, the aratio and rratio are both greater than $\frac{1}{2}$ maximum, namely, "$\frac{1}{2}$ of its base value" ("selected base"). Such a channel is considered to show a concordant pattern. The concordance quantification score is then equal to the cumulative elevation above the $\frac{1}{2}$ power level for the two normalized values, as can be expressed by the form:

$$\text{concordance score} = (\text{rratio} - 0.5) + (\text{aratio} - 0.5).$$

A large concordance score describes the condition of a channel with a high power signal that is confined mostly to a given frequency band.

The concordance and discordance values can be expressed in terms of a mathematical derivation. This derivation is set out as follows:

Let $a_{ch,f}$ = absolute power in channel ch at frequency band f. Typically, ch is in the range 1 to 20 in 20 channels of EEG data, and f represents the frequency bands delta, theta, alpha, beta Then $r_{ch,f}$ = relative power in channel ch at frequency band f $$= \frac{a_{ch,f}}{\sum_{i}^{\text{all bands}} a_{ch,i}}$$

Define $a_{max\,f}$ = maximum absolute power in frequency band f, of all channels
$r_{max\,f}$ = maximum relative power in frequency band f, of all channels.

Normalized values of "aratio" and "rratio" are formulated:

$$aratio_{ch,f} = \frac{a_{ch,f}}{a_{max\,f}}$$

$$rratio_{ch,f} = \frac{r_{ch,f}}{r_{max\,f}}$$

These normalized values are then compared with a threshold level, e.g., half-maximal values, i.e., the selected base value:

If $(aratio_{ch,f} < 0.5)$ and $(rratio_{ch,f} > 0.5)$ then channel ch is termed "discordant" in frequency band f;

If $(aratio_{ch,f} > 0.5)$ and $(rratio_{ch,f} > 0.5)$ then channel ch is termed "concordant" in frequency band f.

For concordance or discordance, the magnitude of the quantification score can be calculated by the formula:

$$score = |rratio - 0.5| + |aratio - 0.5|$$

where | | denotes the absolute value, and 0.5 represents the normalized ½ maximum value.

A typical calculation of quantified values is set out:

Discordant Site
 aratio = 0.3
 rratio = 0.7
 aratio < 0.5 and rratio > 0.5
  so discordance value = 0.2 + 0.2 = 0.4

Concordant Site
 aratio = 0.7
 rratio = 0.8
 aratio > 0.5 and rratio > 0.5
  so concordance value = 0.2 + 0.3 = 0.5

In some situations, it is productive to consider a "selected base" level other than ½ the maximum power values. For example, if a recording is notable for a single channel with much higher power than the others, this atypically high value skews the basis of a comparison scale. Such a value would be discarded as an atypical value or outlier.

A threshold of 40% or 30% of the normalized maximum of 1 could yield more useful sets of discordance and concordance comparisons in different situations. Similarly, situations could arise where the threshold level is set at 60% or 70% of the normalized maximum. Such 40%, 30%, 60% or 70% values would be the "selected base."

With the quantitative EEG results, the cordance mapping is topographically illustrated in a primary frequency domain in FIGS. 1A, 2A, 3A, 4B, 5B, 6C, 6D, 7B and 8B, respectively. Each respective domain is illustrated as the delta, theta, alpha or beta ranges in each of the respective FIGS. 1A, 2A, 3A, 4B, 5B, 6C, 6D, 7B and 8B, respectively, as indicated. The most informative cordance map is usually in the theta or delta frequency bands. The data are obtained from the 20 electrodes connected to the EEG unit which measure the electrical activity in the head.

Information is obtained that may indicate the disconnection of cerebral cortex from the fibers that connect brain regions one to another. This may be the common denominator in Alzheimer's disease, Pick's disease, multi-infarct dementia and multiple sclerosis. In these diseases, gradual severing of the connections that link different brain areas eventually may cause the symptoms of mental and neurological disability. The representative values as given by the discordance and concordance representative values in the cordance maps of FIGS. 1 to 8 as a determination of the electrical output of these regions of the brain provides useful interpretive data to enable the evaluation of the diseases.

The results for the brain region depicted in FIGS. 1 through 8 were obtained from measuring EEG data on subjects in a supine position with eyes closed. Electrodes were applied in the standard 20 locations on the head. At least 30 seconds of relatively artifact free EEG measurements of distribution were effected. The electrodes were applied using standard clinical procedures and the data obtained were stored on an EEG unit.

In this example as illustrated, the EEG unit employed was a system known as QSI 9000 produced by Quantified Signal Imaging, Inc. of Toronto, Ontario, Canada. This system provides data relating to conventional qEEG information, topographical mapping of four frequency bands in the central, frontal, temporal, parietal, and occipital brain regions. Absolute power and relative power data for the different frequency domains are obtained from the EEG measurements.

The avoidance of inaccurate data readings from electrodes about the head can be avoided by using different relationships between any number of selected electrode channels. Computing vector relationships between selected electrodes avoids the effect of referential monopolar values relative to reference electrodes set up in adjacency with the ears of a subject. As such, it has been common in EEG determinations to use monopolar referencing by having a linked ears reference electrode: this means by having electrodes in adjacency to each ear relatively linked. Use of referential monopolar data for the purpose of calculating concordance and discordance creates inaccuracies in cordance calculations having to do with interelectrode distances. While relative power calculations are unaffected by the montages selected, absolute power changes are in proportion to the square of the interelectrode distance. Thus, the frontal and occipital power estimates are inflated, since these are the furthest points from the reference electrodes. Temporal power is underestimated since this region is closest to the reference electrodes.

A configuration is described with reference to FIG. 9 to eliminate this problem. Absolute power data collected from the linked ears reference montages are first reformatted. This is effected using vector calculations set up in a grid of bipolar electrode data, comprising equally-spaced pairs of longitudinal and transverse electrode chains. Power for each individual electrode is then recalculated by averaging power for all respective pairs of electrodes in the chain longitudinally and transversely. Each pair of electrodes in the chain is regarded as a bipolar pair. The concordance and discordance for each individual electrode may be calculated from the data from the bipolar pairs either before averaging, or from the individual electrodes after averaging. The data are then employed to establish the maximum, midpoint and other values as necessary.

As an example with reference to FIG. 9, the electrodes 11, 12, 13, 14 and 15 are set out in the first line, 16, 17, 18, 19 and 20 in a second line, and 21, 22, 23, 24 and 25 in a third line. The ears 26 and 27 are indicated relative to nose 28. In a linked ear montage, each of the electrodes 11 to 25 is referenced to the ears 26 and 27 which are "electrically" linked as a reference. The grid of bipolar electrodes is established along the line defined by electrodes 11 to 15, 16 to 20, and 21 to 25. The vertical grid is 11, 16 and 21; 12, 17 and 22, for example. The bipolar data are set up by measuring the data from each electrode in relation to the adjacent electrodes. As such, for example, the power is measured for electrode 18 relative to electrodes 17, 13, 19 and 23. This is repeated for each electrode relative to its adjacent vertical and transverse electrodes. By computer calculation, the calculations are effected to obtain a measure of electrical activity at each electrode and have a power estimate in the region of the brain. This bipolar electrode montage avoids artifacts caused by the linked ear montage.

This reformatting method effectively standardizes electrode distances and may yield information about longitudinally-oriented and transversely-oriented recording vectors. It is sometimes helpful to map concordance and discordance for differently oriented generators (or fiber tracts) on separate maps. In other circumstances, it is helpful to calculate concordance and discordance after the bipolar data have already been recalculated back to the monopolar format.

The electrode head box which is positioned near the subject contains 20 channels of optically isolated amplifiers. When the patient is prepared, a keyboard command records data from all 20 analog channels. EEG information is then selected for Fast Fourier Transform calculation. Power and spectral amplitudes are calculated for absolute power and relative power and the results of the Fast Fourier Transform are set out in a tabular value of absolute power and relative power.

After analyzing the EEG using the Fast Fourier Transform, the operator generates a topographic map of absolute power, relative power and a cordance map for each of the four conventional EEG frequency bands, namely, the selected primary frequency domain. The data can be stored or displayed on screens or hard copy in a conventional manner.

As illustrated in the flow diagram of FIG. 9, the conventional qEEG maps are obtained from the absolute power and relative power values. The absolute power is optionally subjected to the process for standardizing the electrode distances by the bipolar montage. Thereafter, the absolute power is normalized to establish the maximum absolute power value, namely, the aratio. The midpoint value is established and thereafter, calculations of departures upwardly or downwardly from the midpoint value are determined. The relative power value is normalized by establishing the maximum relative power value, namely, the rratio. The midpoint value is established and thereafter, relative power values upwardly or downwardly departing from the midpoint value are established. From this data, respective discordance maps can be obtained in selected frequency bands or concordance maps obtained in selected frequency bands. The discordance map and concordance map can be merged into a cordance map as indicated.

Figure 10:
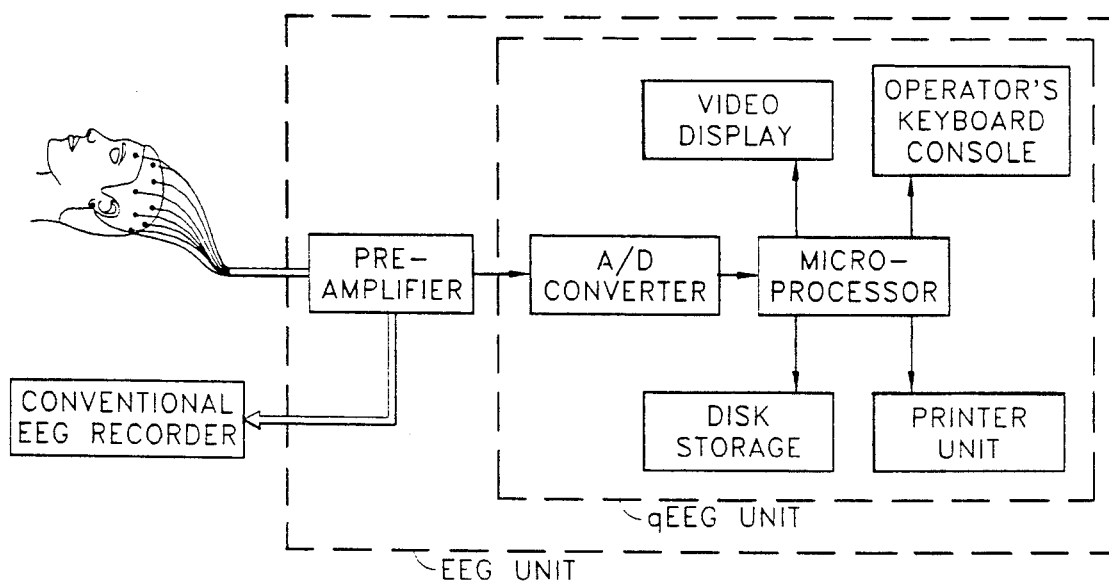
FIG. 10 is a block schematic illustrating the relationship of a patient relative to apparatus for obtaining cordance mapping.
Figure 11D:
Figure 11C:
Figure 11B:
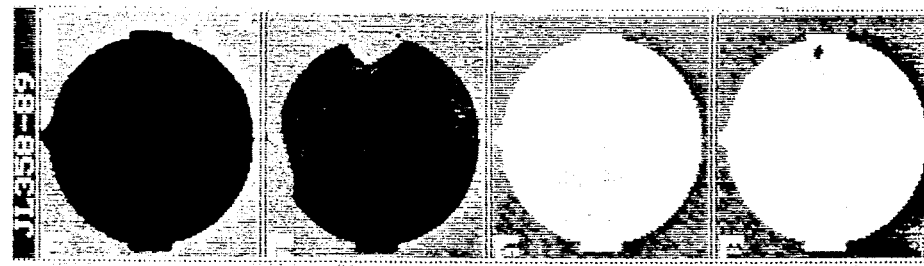
Figure 11A:
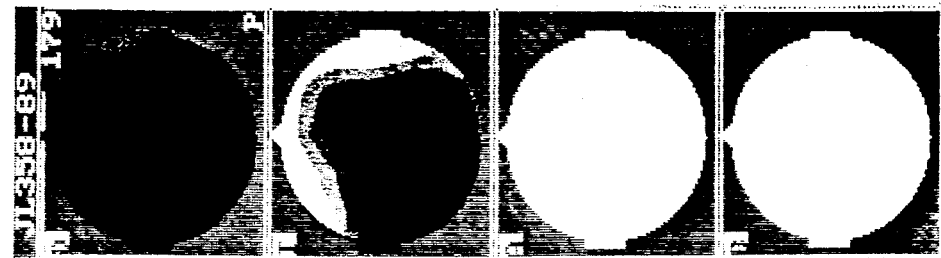

In FIG. 10, there is illustrated a sample EEG unit. The electrode head box is shown connected with the head of the patient whereby power measurements can be taken from the brain of the patient. These are fed to the preamplifier and from such an amplifier, conventional EEG data would be recorded. This would constitute a conventional EEG unit. Specialized within that construction are the elements for a qEEG unit. Data from the preamplifier would be directed to the analog to digital converter and, in turn, to a microprocessor. The processor is operated by a keyboard console and the output can be directed to a video display, storage or printer unit. The microprocessor would operate in terms of the invention to generate the appropriate standardized values, normalization, selected base values, departures from the selected base values, discordance and concordance calculations as indicated in FIG. 9.

FIGS. 11 and 12 are illustrative of the different cordance maps obtained for the same patient in respectively the bipolar montage and the linked ear montage. Illustrated in FIGS. 11A, 11B, 12A and 12B, respectively, are the absolute power and relative power in each of the four frequency bands, theta, delta, alpha and beta. In FIGS. 11C and 12C, there are discordance maps in four frequency bands and in FIGS. 11D and 12D, there are concordance maps in four frequency bands.

An exemplary data Table I for patient JL is set out below. Table I includes the data for the frequency bands delta, theta, alpha and beta in a bipolar montage. In each such band, there is set out the absolute power, relative power and respective discordance or concordance value. Readings from electrodes of an EEG unit have been taken. These discordance and concordance values are topographically depicted as cordance maps illustrated in FIG. 11.

TABLE I

| | DELTA FREQUENCY BAND | | | | THETA FREQUENCY BAND | | | |
|---|---|---|---|---|---|---|---|---|
| | Absolute Power | Relative Power | Discordance | Concordance | Absolute Power | Relative Power | Discordance | Concordance |
| $F_1$ | 45.300 | 53.6 | 47.2 | | 22.800 | 27.0 | 36.3 | |
| $F_2$ | 48.300 | 58.8 | 53.0 | | 21.030 | 25.5 | 35.2 | |
| $F_3$ | 28.925 | 45.3 | 48.7 | | 21.725 | 34.0 | 54.9 | |
| $F_4$ | 40.225 | 54.2 | 52.4 | | 22.075 | 29.7 | 43.9 | |
| $F_7$ | 44.560 | 48.4 | 39.2 | | 28.800 | 31.3 | 39.1 | |

TABLE I-continued

| | | | | | | | | |
|---|---|---|---|---|---|---|---|---|
| $F_8$ | 50.400 | 51.9 | 39.6 | | 20.267 | 20.9 | 24.8 | |
| $C_3$ | 56.700 | 45.9 | | | 33.975 | 27.5 | 23.3 | |
| $C_4$ | 57.175 | 51.1 | | | 28.275 | 25.3 | 25.1 | |
| $T_3$ | 70.133 | 48.9 | | 47.6 | 49.433 | 34.3 | | 47.3 |
| $T_4$ | 72.400 | 45.0 | | 43.2 | 28.033 | 17.4 | | |
| $T_5$ | 69.767 | 49.6 | | 48.4 | 50.067 | 35.6 | | 50.8 |
| $T_6$ | 64.800 | 55.0 | | 52.7 | 28.067 | 23.8 | 21.8 | |
| $P_3$ | 54.250 | 37.4 | | | 59.700 | 41.1 | | 76.7 |
| $P_4$ | 64.075 | 56.2 | | 54.3 | 34.075 | 29.8 | 28.7 | |
| $O_1$ | 106.630 | 51.2 | | 85.3 | 77.860 | 37.2 | | 90.5 |
| $O_2$ | 103.667 | 59.8 | | 97.2 | 50.233 | 29.0 | | 34.9 |
| $F_Z$ | 35.700 | 49.2 | 48.9 | | 27.000 | 37.2 | 55.9 | |
| $C_Z$ | 53.625 | 40.1 | | | 47.750 | 35.7 | | 48.1 |
| $P_Z$ | 76.800 | 43.5 | | 44.9 | 65.650 | 37.2 | | 74.8 |

| | ALPHA FREQUENCY BAND | | | | BETA FREQUENCY BAND | | | |
|---|---|---|---|---|---|---|---|---|
| | Absolute Power | Relative Power | Discordance | Concordance | Absolute Power | Relative Power | Discordance | Concordance |
| $F_1$ | 6.000 | 7.1 | 17.3 | | 10.400 | 12.3 | | |
| $F_2$ | 4.500 | 5.5 | | | 8.375 | 10.2 | | |
| $F_3$ | 6.350 | 10.0 | 36.6 | | 6.825 | 10.7 | | |
| $F_4$ | 5.025 | 6.8 | 20.7 | | 6.950 | 9.4 | | |
| $F_7$ | 8.350 | 9.1 | | | 10.300 | 11.2 | | |
| $F_8$ | 4.900 | 5.0 | | | 21.467 | 22.1 | 26.1 | |
| $C_3$ | 16.450 | 13.3 | | 98.5 | 16.275 | 13.2 | | |
| $C_4$ | 7.375 | 6.6 | | | 19.050 | 17.0 | 15.5 | |
| $T_3$ | 12.500 | 8.7 | | 40.2 | 11.333 | 7.9 | | |
| $T_4$ | 6.433 | 4.0 | | | 54.100 | 33.6 | | 100.0 |
| $T_5$ | 12.867 | 9.1 | | 45.6 | 8.067 | 5.7 | | |
| $T_6$ | 6.300 | 5.3 | | | 18.727 | 15.9 | | |
| $P_3$ | 16.700 | 11.5 | | 86.3 | 14.530 | 10.0 | | |
| $P_4$ | 8.650 | 7.6 | | | 7.300 | 6.4 | | |
| $O_1$ | 15.260 | 7.3 | | | 9.400 | 4.5 | | |
| $O_2$ | 12.500 | 7.2 | | | 7.060 | 4.1 | | |
| $F_Z$ | 5.100 | 7.0 | 22.2 | | 4.700 | 6.5 | | |
| $C_Z$ | 14.000 | 10.5 | | 62.3 | 18.500 | 13.8 | | |
| $P_Z$ | 16.500 | 9.4 | | 69.0 | 17.400 | 9.9 | | |

SUBJECT JL - REFORMATTED BIPOLAR DATA COMPUTATIONS
DELTA, THETA, ALPHA AND BETA BANDS
ABSOLUTE POWER, RELATIVE POWER, DISCORDANCE SCORE, CONCORDANCE SCORE
CORDANCE SCORES LESS THAN 10 ARE OMITTED

An interpretation of the electric output in the brain region and diagnosis is set out for FIGS. 1 through 8.

Figure 12D:
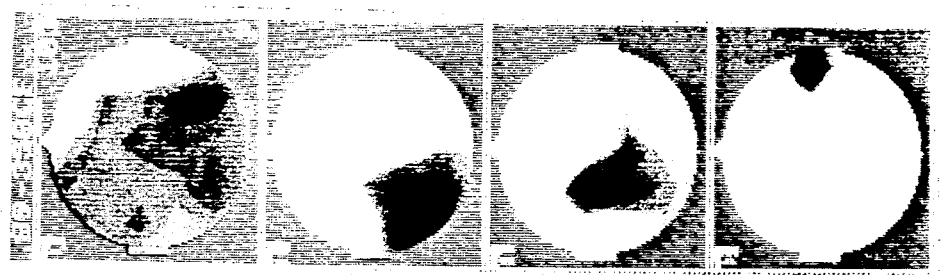
Figure 12C:
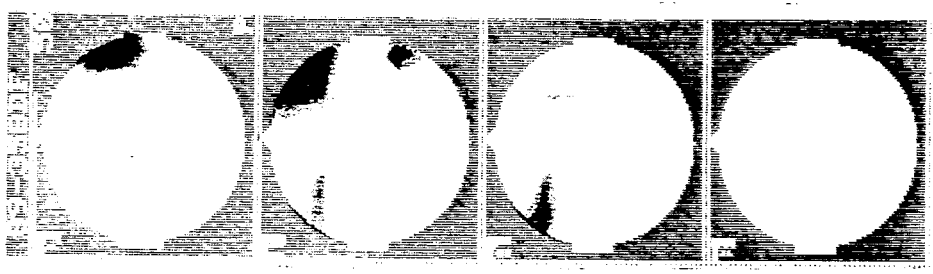
Figure 12B:
Figure 12A:
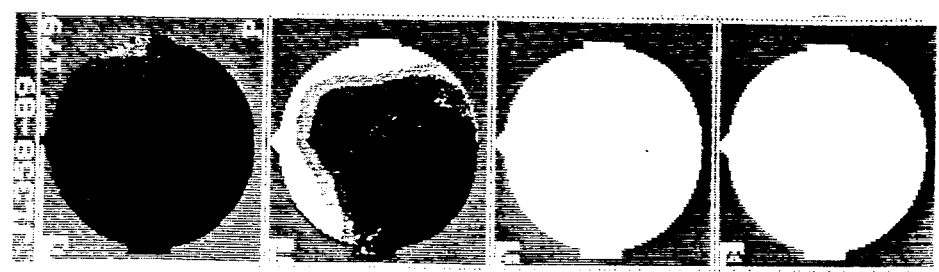

In FIG. 1, the brain imaging studies are for subject JL, a 67 year-old male with multi-infarct dementia. The cordance brain maps (FIG. 1A) show discordance in the delta and theta bands. The MRI scan (FIG. 1B) is a T2-weighted image showing three discrete white-matter lesions separated from the ventricles, that correspond with the areas of discordance (highlighted with arrows). The SPECT scan (FIG. 1C) shows three prominent areas of hypoperfusion that also correspond with the areas of discordance (highlighted with arrows). Absolute power mapping and relative power mapping, which are shown in FIGS. 12A and 12B respectively do not provide this information. Brain maps represent the head as viewed from above, while MRI and SPECT scans represent the head as viewed from below.

The discordance as illustrated in FIG. 1A is closely associated with the presence of deep white-matter ischemic lesions detected by MRI. The decreased absolute slow wave power and increased relative slow wave power seen in the electrodes overlying deep white-matter lesions is demonstrated graphically in FIG. 1A. The discordance map of FIG. 1A shows an intense area of discordance in the delta band in the right frontal region. Three areas of discordance also are seen in the theta band with the largest and most intense focus present in the right frontal region. These areas of discordance coincide closely with three deep white-matter ischemic lesions seen on a T2-weighted MRI scan. In the MRI images, right and left are reversed compared to brain maps. The single largest deep white-matter lesion seen on MRI (right frontal region) corresponds to the largest and most intense area of discordance, seen in both the delta and theta bands. The ischemic nature of these lesions is confirmed by the subject's SPECT scan, which shows areas of diminished perfusion in the right and left frontal and right posterior head regions over the deep white-matter lesions (FIG. 1C; same right-left orientation as MRI). More associations may be determined from the brain cordance map.

Figure 2B:
Figure 2A:
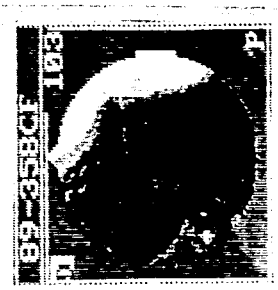

In FIG. 2, there are additional brain imaging studies for subject JL. The cordance brain map (FIG. 2A) shows an intense area of concordance in the delta band in the right posterior head region. The MRI scan (FIG. 2B) is a T1-weighted image showing focal atrophy and ex vacuo ventricular enlargement in the right posterior head region, suggesting an infarction involving the cerebral cortex and corresponding with the area of concordance (highlighted with arrow). The SPECT scan (FIG. 2C) shows a prominent are of hypoperfusion that also corresponds with the area of concordance (high-lighted with arrow). Absolute power mapping and relative power mapping, which are shown in FIGS. 12A and 12B respectively do not provide this information. Brain maps represent the head as viewed from above, while MRI and SPECT scans represent the head as viewed from below.

Concordance is associated with several conditions including infarctions with cortical involvement. Interestingly, SPECT scanning may have difficulty distinguishing between ischemia that is due to deep white-matter ischemic lesions or to infarction with cortical involvement. Cordance mapping yields additional valuable diagnostic information about the nature of these lesions.

Accordingly, discordance is associated with deep white-matter lesions and concordance is associated with infarction with cortical involvement.

Figure 3C:
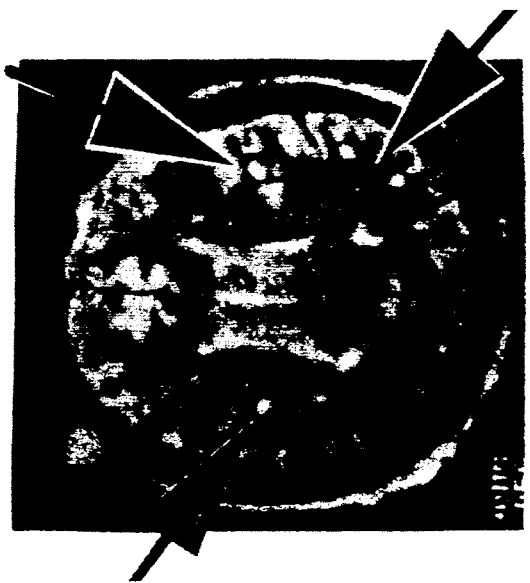
Figure 3B:
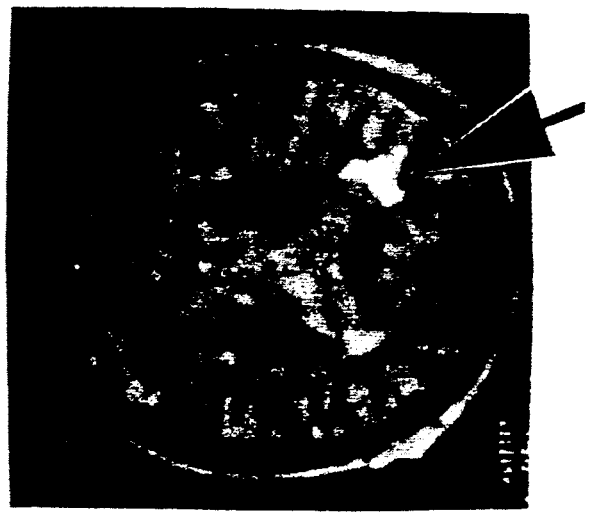
Figure 3A:
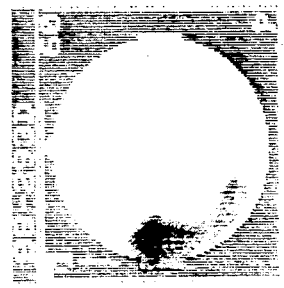

In FIG. 3, there are the brain imaging studies for subject RC, a 67 year-old female with dementia of unknown etiology. The cordance brain map (FIG. 3A) shows a broad area of intense discordance in the delta band in the left posterior head region. The first MRI image (FIG. 3B) is a T2-weighted axial view showing a large patch of presumed deep white-matter ischemic disease in the left posterior head region adjacent to the ventricular horn, that corresponds with the intense discordance (highlighted with arrow). A second MRI image (FIG. 3C) shows multiple punctate areas of presumed ischemic disease that also correspond with areas of discordance (highlighted with arrows). Absolute power mapping and relative power mapping do not provide this information. Brain maps represent the head as viewed from above, while MRI scans represent the head as viewed from below.

The sensitivity of the cordance technique to the presence of smaller lesions is demonstrated by the case of subject RC, whose cordance maps are shown in FIG. 3A. The less intense area of discordance over the right temporal region coincides with a few scattered punctate ischemic lesions seen deep below the temporal cortex (FIG. 3C).

Figure 4A:
Figure 4B:
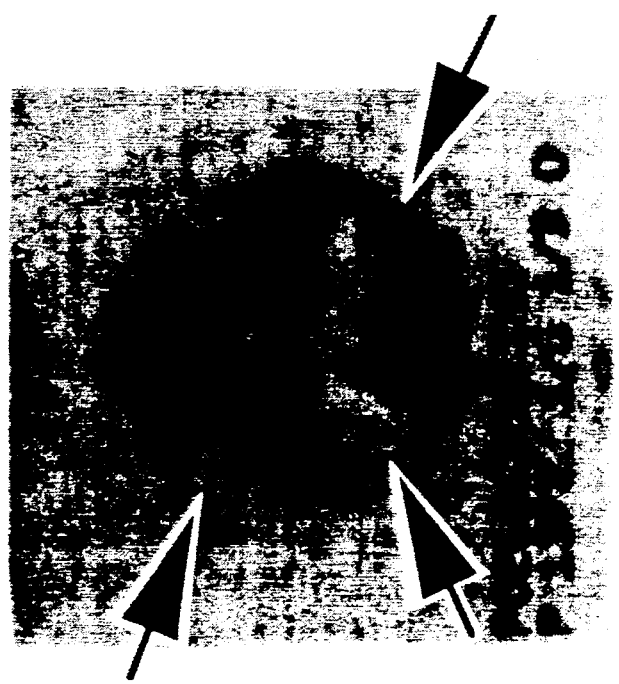
Figure 6D:
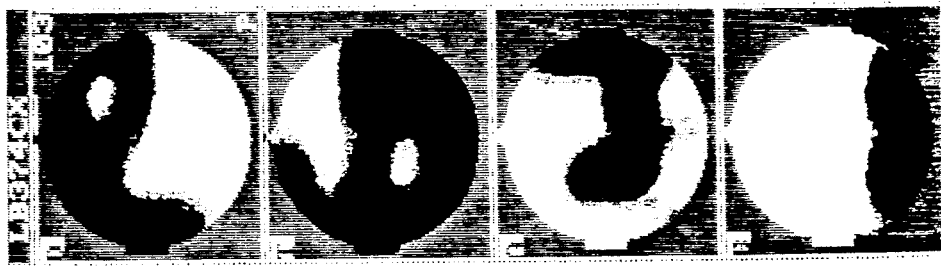
Figure 6C:
Figure 6B:
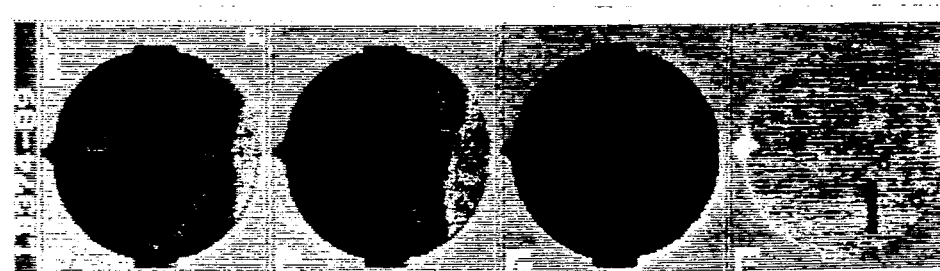
Figure 6A:
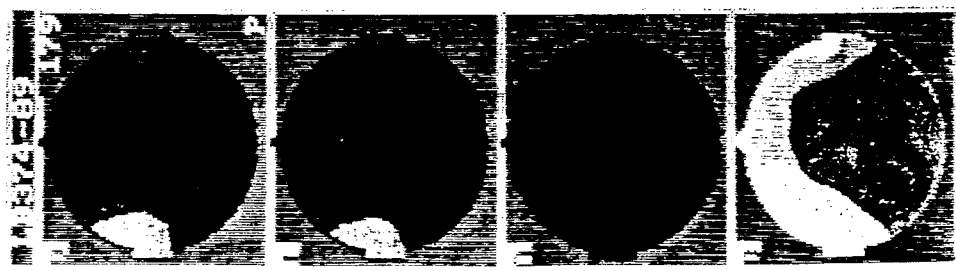

FIG. 4 are the scans of GK, an 87 year old male who presented with prominent memory loss and word-finding difficulties. He was given provisional diagnosis of Alzheimer's disease. A PET scan, FIG. 4A, shows prominent biparietal hypometabolism, as well as right frontotemporal hypometabolism (arrows). The discordance map for the same subject (FIG. 4B) shows biparietal discordance, more prominent on the right, corresponding to the PET pattern. In addition, there is a right frontotemporal focus of discordance correlating with the PET scan (arrows). The PET scan shows the brain as viewed from below, while the discordance map shows the brain as viewed from above.

FIG. 5 depicts scans of LB, a 51 year old female with a diagnosis of Pick's disease. A SPECT scan (FIG. 5A) highly suggests this diagnosis, with prominent and severe frontal hypoperfusion (arrows). The discordance map (FIG. 5B) shows intense bilateral frontal discordance (arrow). The SPECT scan is viewed from below, and the discordance scan is viewed from above.

FIG. 6 is additional brain imaging studies for subject LB. In FIG. 6A, the brain maps of absolute power are shown in the delta, theta, alpha, and beta bands (from top). FIG. 6B shows the maps of relative power in the same frequency bands. Both of these columns show a diffuse excess of slow-wave activity that does not have any clear regional predominance. The map in FIG. 6C is a discordance map of the same subject, showing clear and prominent frontal discordance in the theta band most prominently, and most significantly affecting the right hemisphere. In the map in FIG. 6D, there is a diffuse concordance that is usually bilaterally symmetric, and is of no significance in this case.

FIG. 7 illustrates a scan of SE, a 26 year old white male with multiple sclerosis. The MRI scan (FIG. 7A) shows a single large demyelinating lesion underlying the left frontotemporal cortex (arrow). The discordance map (FIG. 7B) shows a prominent area of discordance in the left frontotemporal region. The MRI shows the brain as viewed from below, while the discordance map shows the brain as viewed from above.

FIG. 8 shows scans for PH, a 76 year old male control subject with deep white-matter ischemic lesions in the frontal lobes. A HMPAO SPECT scan for the subject (FIG. 8A) shows globally diminished cerebral perfusion, with the most striking decreases seen in the frontal lobe (arrows). FIG. 8B shows a discordance map for this same subject, with at least mild discordance in most brain regions, and prominent frontal discordance corresponding to the areas of greatly diminished perfusion (arrows). The SPECT scan is viewed from below, while the discordance map is viewed from above.

The cordance mapping is used to assess the presence and nature of brain lesions. The data obtained by the cordance mapping conforms substantially and equivalently to the data obtained by the MRI scan, PET or SPECT scan as illustrated in the figures. The values representative of the combination of the absolute power data and relative power data provide for cordance brain mapping. Such mapping thus provides a valuable advance. Absolute power and relative power mapping considered separately does not provide these data. It is thus possible with the cordance brain mapping technique using the quantitative EEG data to obtain effective information to facilitate evaluation of electrical output of the brain, and hence the presence and nature of disease conditions.

It may be unnecessary to resort to the relatively expensive SPECT and PET techniques. The diseases represented by the information obtained by cordance brain mapping are the result of deep lesions in the brain that produce excessive delta and theta slow wave activity in an EEG. Detection of these lesions by conventional EEGs or currently available methods of qEEGs is not possible. Thus, a conventional qEEG would provide only data about absolute power and about relative power independently. From such unrelated data, it is not possible to obtain the same information as cordance mapping to assist in characterizing the human brain.

The quantified methods increase the sensitivity of the EEG and the cordance mapping extends this sensitivity to provide useful information. The examination of the cordance map distribution of the absolute power and relative power in the delta and theta bands particularly over the surface of the brain provides useful information. The discordance and concordance values are determined by a calculation of the comparison of the individual electrode absolute and relative power with the maximal absolute and maximal relative power values over the whole brain. A brain region shows a discordant pattern in a given frequency band if the relative power from the corresponding electrode is increased above half the maximum relative power value for the subject while the absolute power is decreased below half the maximum absolute power value of the subject. Conversely, the brain region shows a concordance pattern where both the absolute power and relative power value from the site are increased about the half maximal values of that subject.

The sensitivity and specificity of both discordance and concordance may be adjusted by changing the thresholds at which the two measures are defined. By requiring that concordant increases in absolute and relative power be 5%, 10%, or 20% above the half-maximal value ("selected base") for that subject, the specificity of the measure may be increased. Similarly, by requiring that discordant absolute and relative power be separated by large differences, the specificity of the discordance measure may be increased. There are other parameters that may be adjusted as well. For example, the half-maximal value may be calculated in several different ways. It may be based on half-maximal value from all regions for that individual subject, the mean or median value for that subject, or a half-maximal value after the 1 or 2 highest values (which may be outliers) have been eliminated. These further adjustments may change the sensitivity, specificity, or usefulness in different clinical situations.

Cordance mapping has been developed on the population of mostly elderly subjects with possible organic mental syndromes, as well as young adults with multiple sclerosis. There are a number of other possible applications for this technique among young and older adult populations as well. Possible other applications include populations at risk for deep brain tumors, such as patients with a history of brain tumor who are being monitored for possible recurrence, patients with AIDS who are at risk for central nervous system lymphoma, multiple sclerosis, patients with epilepsy, and other brain diseases.

Applications of the invention relate to different fields of neurophysiology. The cordance mapping can be continually monitored during medical procedures such as surgery or in treatment in intensive care units. Similarly, during treatment of patients changes in the mapping would indicate data relating to the effectiveness of treatment, or improvement or deterioration of subjects. The cordance mapping techniques can be used to determine or assess the brain in accident situations or diseases such as cerebral vascular diseases or strokes which may be the result of genetic or developmental-congenital problems, traumatic head injury, exposure to toxic agents or the product of other pathogenic physiological processes such as elevated blood pressures, stress responses, and arterial blockages.

It should be possible with cordance methods to facilitate diagnosis of epilepsy, substance abuse, genetic disorders, diseases of the kidney or liver affecting brain function, sensitivities relating to food and odor which correlate with behavioral changes, illnesses accompanied by high fevers, viral or bacterial infection, sensory or motor handicaps which would include visual handicaps, auditory and motor handicaps, learning disabilities, psychiatric disorders, headaches, cyclical hormonal reactions, and other dysfunctions.

This invention has application to any disease state that affects the afferent fibers that originate in or connect to the cerebral cortex, either at the cortical, subcortical white-matter, or subcortical grey matter level. Therefore, patients with epilepsy who have cortical or subcortical dysfunction, patients with inheritable diseases that affect brain function at the cortical or subcortical level, as well as tumors, trauma, or infectious processes that might affect brain function all may be usefully evaluated using cordance mapping.

By this invention, there is provided a method, apparatus, and system for obtaining useful assessment and diagnosis of the brain based upon electrical activity.

Many other examples of the invention exist each differing from another in matters of detail only. For instance, although the data have been set out as power, it is possible that other representations of energy can be used. This could be voltage, amplitude, or coherence. Although each of the first data and second data are defined relative to their own base value, it may be possible to have a common base value.

Also, whereas the primary frequency domain is described as essentially a single frequency band of the total relevant spectrum of the four conventional bands from zero to greater than about 12 Hz, the primary frequency domain could be differently defined. It could be more than any one of the four frequency bands. Also, the secondary frequency domain may be greater or less than any one of the four conventional frequency bands.

Similarly, the time interval evaluation of 4-second periods for measuring data in each of the channels may be different. In different situations, data from a different number of selected electrode channels may be used to generate the appropriate first data and second data in the different frequency domains.

Also, although the concordance has been described with reference to increases in a percentage proportional or fractional value of a base value, it is possible that a concordance value where both first and second data are lower than this base value can be used. Also, although the system has been described with reference to 20 channels, more or less channels may be used. It is possible, for instance, to increase the number of channels to at least about 128. Indeed, it is possible that the greater the number of channels, the greater the amount of data will be obtained. This should provide for more effective analysis.

Different techniques can be used to overcome the artifacts caused by linked ear reference montage. For instance, compensation factors can be ascertained and applied for different power intensities and/or electrode distances in each brain region. This application can be computed into the absolute power determinator to permit establishing the appropriate referential value.

The invention is defined in the following claims.

We claim:

1. A method of determining the electrical output of a brain region in the head of a subject comprising obtaining first data representative of energy in the brain region in a primary frequency domain, determining second data representative of energy in the primary frequency domain substantially simultaneously relative to the energy in a secondary frequency domain, and relating the first data with the second data thereby obtaining a value representative of electrical output in the brain region.

2. A method of determining the electrical output of a brain region in the head of a subject comprising obtaining first data representative of energy in the brain region in a primary frequency domain, determining second data representative of energy in the primary frequency domain relative to the energy in a secondary frequency domain, and relating the first data with the second data thereby obtaining a value representative of electrical output in the brain region, wherein relating is effected by determining the first data and second data relative to a selected base value and wherein when the first data and the second data both increase or decrease relative to the selected base value, a concordance condition is indicated, and wherein when one of the first data and the second data respectively increase or decrease relative to the selected base while the other of the first data or second data, respectively, is oppositely directed relative to the selected base, a discordance condition is indicated.

3. A method as claimed in claim 2 including providing a selected base for the first data and a selected base for the second data.

4. A method as claimed in claim 2 wherein the first data are compared to a selected base value of the first data and the second data are compared to a selected base value of the second data thereby to obtain respectively either the concordance or discordance indication, and wherein the discordance and concordance is established in the primary frequency domain.

5. A method as claimed in claim 2 including obtaining a quantified value of the amount of departure of the discordance indication and the concordance indication by determining the amount of departure from the selected base.

6. A method as claimed in claim 5 including mapping topographically the quantified value over the brain region.

7. A method as claimed in claim 5 including having multiple primary frequency domains and including mapping the quantified value for multiple primary frequency domains.

8. A method as claimed in claim 5 including displaying a topographical map of the quantified value in a primary frequency domain.

9. A method as claimed in claim 5 wherein the primary frequency domain includes at least one of a delta region and a theta region.

10. A method as claimed in claim 2 wherein the first data are obtained from energy measured by selected electrode channels, and locating the selected electrode channels strategically about the brain.

11. A method as claimed in claim 2 wherein the first data are an absolute power, and the second data are a relative power, the absolute power being power measured by selected electrode channels over the primary frequency domain and the relative power being the distribution of power in the primary frequency domain relative to the power in the secondary frequency domain in the selected electrode channels.

12. A method as claimed in claim 2 including comparing the representative value with a selected base representative of the brain region and assessing from the comparison the physiology in the brain region.

13. A method as claimed in claim 2 including diagnosing from the representative value the existence or nonexistence of a brain lesion characterized by at least one of the disorders indicated by dementia, such disorders being selectively multi-infarct dementia, Alzheimer's disease, Pick's disease or a demyelinating disease, selectively, multiple sclerosis.

14. A method as claimed in claim 2 including normalizing the effect of a selected energy distribution in the brain region, such region being selectively adjacent to at least one of the ears of the subject, the normalizing being effected by determining an energy measurement of different electrodes relative to data of at least one other electrode.

15. A method of determining the electrical output of a brain region in the head of a subject comprising obtaining first data representative of energy in the brain region in a primary frequency domain, determining second data representative of energy in the primary frequency domain relative to the energy in a secondary frequency domain, and relating the first data with the second data thereby obtaining a value representative of electrical output in the brain region, wherein the first data are divided by a selected first data value, and the second data are divided by a selected second data value thereby to obtain a normalized base value for normalizing the first data, and a normalized base for normalizing the second data, respectively, and wherein the first data relative to the normalized base value of the first data and the second data relative to the normalized base value of the second data yields concordance and discordance indications.

16. A method as claimed in claim 15 including employing a selected percentage of the normalized base value of the first data as a first selected base value, and employing a selected percentage of the normalized base value of the second data as a second selected base value and wherein when the first data are relatively less than the first selected base value and the second data are relatively greater than the second selected base value, respectively, a discordance is indicated, and wherein when the first selected data is increased relative to the first selected base value and the second data is relatively increased relative to the second selected base value, a concordance is indicated.

17. A method of determining the electrical output of a brain region in the head of a subject comprising obtaining first data representative of energy in the brain region in a primary frequency domain, determining second data representative of energy in the primary frequency domain relative to the energy in a secondary frequency domain, and relating the first data with the second data thereby obtaining a value representative of electrical output in the brain region, wherein the first data are an absolute power, and the second data are a relative power, the absolute power being power measured by selected electrode channels over the primary frequency domain and the relative power being the distribution of power in the primary frequency domain relative to the power in the secondary frequency domain in the selected electrode channels.

18. A method as claimed in claim 17 wherein relating the absolute power and the relative power is defined by the combination of the absolute power and relative power such that the relative power at a selected primary frequency domain is equal to the absolute power at the selected primary frequency domain divided by the power for the secondary frequency domain.

19. A method of determining the electrical output of a brain region in the head of a subject comprising obtaining first data representative of energy in the brain region in a primary frequency domain, determining second data representative of energy in the primary frequency domain substantially simultaneously relative to the energy in a secondary frequency domain, and relating the first data with the second data thereby obtaining a representative value of electrical output in the brain region, including comparing the representative value with a selected base representative of the brain region and assessing from the comparison the physiology in the brain region.

20. A method as claimed in claim 19 wherein the first data are obtained from energy measured by selected electrode channels, and locating the selected electrode channels strategically about the brain.

21. A method as claimed in claim 20 wherein multiple channels are obtained by locating multiple electrodes over the head of the subject in strategic locations about the head, obtaining data in an analog form from the electrodes, digitizing the analog data from the electrodes, and subjecting the digitized data to Fourier Transformation to obtain absolute power for each channel in the primary frequency domain.

22. A method as claimed in claim 21 including obtaining a relative power for each channel, such relative power being obtained by dividing the absolute power in the primary frequency domain by the absolute power in the secondary frequency domain.

23. A method as claimed in claim 20 wherein the energy is measured by the electrode for each channel, the energy measurement being obtained with reference to at least one other electrode located on the subject.

24. A method as claimed in claim 23 wherein the energy measured by the electrodes for each channel is obtained with reference to multiple electrodes about the head.

25. A method of determining the electrical output of a brain region in the head of a subject comprising obtaining first data representative of energy in the brain region in a primary frequency domain, determining second data representative of energy in the primary frequency domain relative to the energy in a secondary frequency domain, and relating the first data with the second data thereby obtaining a representative value of electrical output in the brain region, including diagnosing from the representative value the existence or non-existence of a brain lesion characterized by at least one of the disorders indicated by dementia, such disorders being selectively multi-infarct dementia, Alzheimer's disease, Pick's disease or a demyelinating disease, selectively, multiple sclerosis.

26. A method of determining the electrical output of a brain region in the head of a subject comprising obtaining first data representative of energy in the brain region in a primary frequency domain, determining second data representative of energy in the primary frequency domain relative to the energy in a secondary frequency domain, and relating the first data with the second data thereby obtaining a value representative of electrical output in the brain region, including normalizing the effect of a selected energy distribution in the brain region, such region being selectively adjacent to at least one of the ears of the subject, the normalizing being effected by determining an energy measurement of different electrodes relative to data of at least one other electrode.

27. A method of determining the electrical output of a brain region in the head of a subject comprising obtaining first data representative of energy in the brain region in a primary frequency domain, substantially simultaneously determining second data representative of energy in the primary frequency domain relative to the energy in a secondary frequency domain, relating the first data with the second data thereby obtaining a value representative of electrical output in the brain region, and obtaining a brain map of the representative value.

28. A method of determining the electrical output of a brain region in the head of a subject comprising obtaining first data representative of energy in the brain region in a primary frequency domain, determining second data representative of energy in the primary frequency domain relative to the energy in a secondary frequency domain, and relating the first data with the second data thereby obtaining a representative value of electrical output in the brain region, and obtaining a brain map of the representative value including obtaining a normalized base value for the first data and a normalized base for the second data respectively, obtaining simultaneously selected base values from the normalized base values and obtaining the representative value based on departures from the selected base values.

29. A method of determining the electrical output of a brain region in the head of a subject comprising obtaining first data representative of energy in the brain region in a primary frequency domain, determining second data representative of energy in the primary frequency domain relative to the energy in a secondary frequency domain, and relating the first data with the second data thereby obtaining a representative value of electrical output in the brain region, and obtaining a brain map of the representative value including comparing the representative value with a simultaneously obtained selected base representative of the brain region and assessing from the comparison the physiology in the brain region.

30. A method of determining the electrical output of a brain region in the head of a subject comprising obtaining first data representative of energy in the brain region in a primary frequency domain, substantially simultaneously determining second data representative of energy in the primary frequency domain relative to the energy in a secondary frequency domain, normalizing the first data, normalizing the second data, selecting a simultaneously obtained base value relative to the respective normalizations, determining departures of the first data and the second data from the respective selected base values, and relating the departures thereby to obtain a brain map representative of electrical output in the brain region.

31. A method of determining the electrical output of a brain region in the head of a subject comprising obtaining first data representative of energy in the brain region in a primary frequency domain, determining second data representative of energy in the primary frequency domain relative to the energy in a secondary frequency domain, normalizing the first data, normalizing the second data, selecting a base value relative to the respective normalizations, determining departures of the first data and the second data from the respective selected base values, and relating the departures thereby to obtain a brain map representative of electrical output in the brain region, including having multiple primary frequency domains and including effecting mapping for the multiple primary frequency domains.

32. A method as claimed in claim 31 including displaying a topographical map of the representative values in a primary frequency domain.

33. A method of determining the electrical output of a brain region in the head of a subject comprising measuring an absolute power in the brain region in a primary frequency domain, substantially simultaneously determining a relative power in the primary frequency domain relative to the absolute power in a secondary frequency domain, normalizing the absolute power, normalizing the relative power, selecting a simultaneously obtained base value relative to the respective normalizations, determining departures of the absolute power and the relative power from the respective selected base values, and relating the departures thereby to obtain a cordance brain map representative of electrical output in the brain region.

34. A method of determining the electrical output of a brain region in the head of a subject comprising measuring an absolute power in the brain region in a primary frequency domain, determining a relative power in the primary frequency domain relative to the absolute power in a secondary frequency domain, normalizing the absolute power, normalizing the relative power, selecting a base value relative to the respective normalizations, determining departures of the absolute power and the relative power from the respective selected base values, and relating the departures thereby to obtain a cordance brain map representative of electrical output in the brain region, including obtaining a topographical map of the representative values in a primary frequency domain.

35. A method as claimed in claim 34 wherein the primary frequency domain includes one of a delta region and a theta region, and the secondary frequency domain is selectively at least both of the delta and theta regions.

36. A method as claimed in claim 35 wherein the absolute power is obtained from selected electrode channels, and locating the selected electrode channels strategically about the brain.

37. Apparatus for determining the electrical output of a brain region in the head of a subject comprising means for obtaining first data representative of an energy in the brain region in a primary frequency domain, means for determining substantially simultaneously second data representative of energy in the primary frequency domain relative to the energy in a secondary frequency domain, and means for relating the first data with the second data thereby obtaining a value representative of electrical output in the brain region.

38. Apparatus as claimed in claim 37 including means for comparing the first data to a simultaneously obtained selected base value of the first data and means for comparing the second data to a simultaneously obtained selected base value of the second data.

39. Apparatus as claimed in claim 37 including electrode channels for location about the head and wherein the first data are absolute power, and the second data are relative power, the absolute power being power from a selected electrode channel over the primary frequency domain and the relative power being the distribution of power in the primary frequency relative to a secondary frequency domain in the selected electrode channel.

40. Apparatus as claimed in claim 39 including means for measuring the energy by the electrode for each channel, and means for obtaining the energy measurement with reference to at least one other electrode about the subject.

41. Apparatus for determining the electrical output of a brain region in the head of a subject comprising means for obtaining first data representative of an energy in the brain region in a primary frequency domain, means for determining second data representative of energy in the primary frequency domain relative to the energy in a secondary frequency domain, and means for relating the first data with the second data thereby obtaining a value representative of electrical output in the brain region, including means for determining a selected base value, the value being selectively normalized, means for relating the first data and second data relative to the selected base value, and means for determining selectively concordance and discordance conditions of the first data and second data relative to the selected base value.

42. Apparatus as claimed in claim 41 including means for determining a selected base value for the first data and a selected base value for the second data.

43. Apparatus as claimed in claim 41 including means for comparing the first data to a selected base value of the first data and means for comparing the second data to a selected base value of the second data.

44. Apparatus as claimed in claim 43 including means for quantifying an amount of a departure of the first data from a selected base value and the amount of departure of the second data from a selected base value.

45. Apparatus as claimed in claim 44 including means for mapping the quantified value over the brain region.

46. Apparatus for the method as claimed in claim 44 including means for selecting multiple primary frequency domains and including means for mapping the quantified value for multiple primary frequency domains.

47. Apparatus for the method as claimed in claim 44 including means for displaying a topographical map of the quantified value in a primary frequency domain.

48. Apparatus as claimed in claim 41 including electrode channels for location about the head and wherein the first data are absolute power, and the second data are relative power, the absolute power being power from a selected electrode channel over the primary frequency domain and the relative power being the distribution of power in the primary frequency relative to a secondary frequency domain in the selected electrode channel.

49. Apparatus for determining the electrical output of a brain region in the head of a subject comprising means for obtaining first data representative of an energy in the brain region in a primary frequency domain, means for determining second data representative of energy in the primary frequency domain relative to the energy in a secondary frequency domain, and means for relating the first data with the second data thereby obtaining a value representative of electrical output in the brain region including means for comparing the first data to a selected base value of the first data and means for comparing the second data to a selected base value of the second data, including means for quantifying an amount of a departure of the first data from a selected base value and the amount of departure of the second data from a selected base value.

50. Apparatus as claimed in claim 49 including means for mapping the quantified value over the brain region.

51. Apparatus for the method as claimed in claim 49 including means for selecting multiple primary frequency domains and including means for mapping the quantified value for multiple primary frequency domains.

52. Apparatus for the method as claimed in claim 49 including means for displaying a topographical map of the quantified value in a primary frequency domain.

* * * * *